United States Patent

Hayase et al.

[11] Patent Number: 5,089,043
[45] Date of Patent: Feb. 18, 1992

[54] HETEROCYCLIC OXY-PHENOXYACETIC ACID DERIVATIVES AND THEIR USE AS HERBICIDES

[75] Inventors: Yoshio Hayase, Kameyama; Kohei Matsumoto, Kusatsu; Kazuo Kamei, Tokyo; Kinya Ide, Kusatsu; Toshio Takahashi, Nishinomiya, all of Japan

[73] Assignee: Shionogi & Co., Ltd., Osaka, Japan

[21] Appl. No.: 610,048

[22] Filed: Nov. 6, 1990

[30] Foreign Application Priority Data

Nov. 9, 1989 [JP] Japan .................... 1-291858

[51] Int. Cl.$^5$ .................... H01N 43/48; H01N 43/40; C07D 241/52; C07D 213/643
[52] U.S. Cl. ............................ 71/90; 71/92; 71/94; 544/60; 544/62; 544/116; 544/131; 544/354; 544/360; 546/291; 560/170; 564/197
[58] Field of Search ............... 544/354, 60, 131, 360; 546/291; 71/92, 94, 90

[56] References Cited

U.S. PATENT DOCUMENTS

| | | | |
|---|---|---|---|
| 3,543,305 | 11/1970 | Neighbors | 71/108 |
| 4,740,235 | 4/1988 | Schurter et al. | 71/94 |
| 4,750,931 | 6/1988 | Rogers | 544/354 |
| 4,832,736 | 5/1989 | Schurter et al. | 71/94 |
| 4,838,930 | 6/1989 | Schurter et al. | 71/94 |
| 4,875,926 | 10/1989 | Schurter et al. | 71/94 |
| 4,948,414 | 8/1990 | Schurter et al. | 71/86 |

FOREIGN PATENT DOCUMENTS

| | | | |
|---|---|---|---|
| 0200677 | 12/1986 | European Pat. Off. | |
| 3132622 | 8/1982 | Fed. Rep. of Germany | |
| 35575 | 2/1982 | Japan | 544/354 |

*Primary Examiner*—Mukund J. Shah
*Assistant Examiner*—E. Bernhardt
*Attorney, Agent, or Firm*—Wenderoth, Lind & Ponack

[57] ABSTRACT

A heterocyclic oxy-phenoxyacetic acid derivative of the formula:

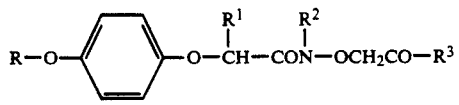

; or its salt, which is useful as a herbicide.

6 Claims, No Drawings

HETEROCYCLIC OXY-PHENOXYACETIC ACID DERIVATIVES AND THEIR USE AS HERBICIDES

The present invention relates to heterocyclic oxy-phenoxyacetic acid derivatives and their use as herbicides.

There are known various heterocyclic oxy-phenoxyacetic acid derivatives, which are commercially available as herbicides. Their typical examples are as follows:

Fluazifop-butyl (JP-A-58-40947):

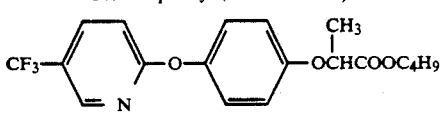
(a)

Piriphenop (JP-A-51-48432):

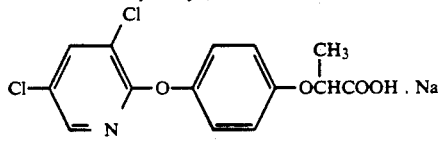
(b)

Haloxyfop-ethoxyethyl (JP-A-54-24879):

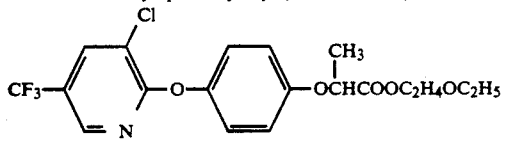
(c)

Quizalofop-ethyl (JP-A-56-46868):

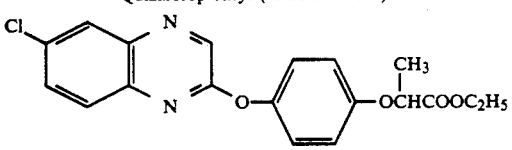
(d)

These heterocyclic oxy-phenoxyacetic acid derivatives are characteristic in producing a strong herbicidal effect against a variety of weeds with weak phytotoxicity on broad-leaved crop plants. However, their intergeneric selectivity on monocotyledonous plants is relatively small so that they sometimes cause phytotoxicity on crop plants such as wheat, barley and rice plants while they do not produce any herbicidal effect on certain perennial weeds. Accordingly, their practical use is restricted as to application field, application mode, etc.

As the result of an extensive study, it has now been found that certain heterocyclic oxy-phenoxyacetic acid derivatives having a fundamental chemical structure corresponding to the condensation product between the carboxyl group of a heterocyclic oxy-phenoxyacetic acid and the amino group of an aminoxyacetic acid produces a remarkable herbicidal activity against a variety of weeds without exerting any material phytotoxicity on broad-leaved crop plants. It is notable that they show a significant intergeneric selectivity on monocotyledonous plants. The present invention is based on the above finding.

The objective compound of the present invention is a heterocyclic oxy-phenoxyacetic acid derivative of the formula:

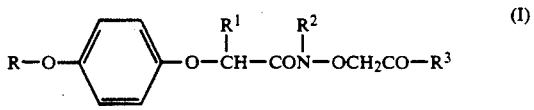
(I)

wherein
R is a pyridyl or quinoxalinyl group optionally bearing thereon not more than two substituents chosen from halogen and halo(lower)alkyl;

$R^1$ and $R^2$ are each hydrogen or lower alkyl; and $R^3$ is —$NR^4R^5$, —$NHR^6$ or —$OR^7$ (in which $R^4$ and $R^5$ are each hydrogen or lower alkyl or, when taken together with the adjacent nitrogen atom, represent a saturated nitrogen-containing 5- or 6-membered heterocyclic group optionally having one additional ring hetero atom chosen from nitrogen, oxygen and sulfur, which may bear thereon not more than two lower alkyl groups; $R^6$ is lower cycloalkyl, substituted or unsubstituted aryl, or a saturated or unsaturated 5- or 6-membered heterocyclic group having at least one ring hetero atom chosen from nitrogen, oxygen and sulfur or a group of the formula: —$NR^8R^9$ (in which $R^8$ and $R^9$ are each hydrogen or lower alkyl or, when taken together, represent a lower alkylidene group); and $R^7$ is hydrogen, lower alkyl, lower alkoxy, substituted or unsubstituted aryl(lower)alkyl, substituted or unsubstituted aryloxy(lower)alkyl, halo(lower)alkyl, hydroxy(lower)alkyl or lower alkoxy(lower)alkyl), or its salts.

In the above significances, the term "lower" is intended to mean a group having not more than 8 carbon atoms, particularly not more than 6 carbon atoms. Examples of "lower alkyl" include methyl, ethyl, propyl, isopropyl, butyl, isobutyl, t-butyl, pentyl, hexyl, etc. As "lower cycloalkyl", there may be exemplified cyclopropyl, cyclobutyl, cyclopentyl, cyclohexyl, etc. "Halogen" includes chlorine, bromine, fluorine and iodine, and preferred are chlorine and fluorine. "Halo(lower)alkyl" covers monochloromethyl, difluorochloromethyl, trifluoromethyl, etc., and preferred is trifluoromethyl. "Aryl" means phenyl, naphthyl, etc. The substituent(s) which may be present on the aryl group are lower alkyl, lower alkoxy, halogen, etc. Examples of the "saturated nitrogen-containing 5- or 6-membered heterocyclic group" are pyrrolidino, piperidino, piperazino, morpholino, thiamorpholino, etc. The "saturated or unsaturated 5- or 6-membered heterocyclic group" may be the one having at least one ring hetero atom, usually one to three ring hetero atoms and preferably one or two ring hetero atoms chosen from nitrogen, oxygen and sulfur in addition to the ring carbon atoms, and its examples are imidazolyl, pyrolyl, pyrrolidyl (including pyrrolidino), pyridyl, piperidyl (including piperidino), pyrazinyl, pyrimidinyl, pyridazinyl, piperazinyl (including piperazino), furyl, morpholynyl (including morpholino), piranyl, thienyl, etc. "Lower alkylidene" includes methylene, ethylidene, vinylidene, propylidene, isopropylidene, butylidene, isobutylidene, pentylidene, hexylidene, etc.

The heterocyclic oxy-phenoxyacetic acid derivative (I) of the present invention may be in a free form or a salt form. When in a salt form, it may be a salt as to the carboxyl group represented by —$COR^3$ or an acid addition salt as to the basic nitrogen atom. Examples of the former salt are an alkali metal (e.g. sodium, potassium) salt, an alkaline earth metal (e.g. calcium, barium, magnesium) salt, an organic amine (e.g. ammonium, diethylamine, triethylamine, pyridine, picoline) salt, etc. Examples of the latter salt are an inorganic acid (e.g. hydrochloric acid, hydrobromic acid, sulfuric acid, phosphoric acid) salt, an organic acid (e.g. acetic acid, propionic acid, oxalic acid, malonic acid, succinic acid, glutaric acid, adipic acid, malic acid, maleic acid, citric acid, benzoic acid, methanesulfonic acid) salt, etc.

The heterocyclic oxy-phenoxyacetic acid derivative (I) can include an asymmetric carbon atom and has its optical isomers. It may be used as a herbicide in a d- or l-form, or in a mixture comprising those forms in an optional proportion.

The heterocyclic oxy-phenoxyacetic acid derivative (I) can be produced by various procedures, among which a typical example comprises reacting a carboxylic acid of the formula:

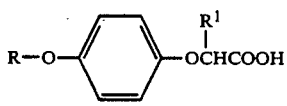

(II)

wherein R and $R^1$ are each as defined above, or its reactive derivative on the carboxy group, with an amine of the formula:

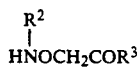

(III)

wherein $R^2$ and $R^3$ are each as defined above.

As the reactive derivative of the carboxylic acid (II) on the carboxyl group, there may be exemplified acid halides (e.g. acid chloride), acid anhydrides, esters, active amides, etc. In case of acid anhydrides, there may be used mixed acid anhydrides with aliphatic acids (e.g. pivalic acid, trichloroacetic acid), dialkylphosphoric acids, dialkylphosphorous acids, alkylcarbonic acids or the like. Examples of the esters are methyl ester, ethyl ester, cyanomethyl ester, p-nitrophenyl ester, N-hydroxysuccinimide ester, etc. As the active amides, there are employed admides with imidazole, alkylimidazole, etc.

When the carboxylic acid (II) itself is reacted with the amine (III), the reaction is normally effected in an inert solvent (e.g. dioxane, methylene chloride, chloroform, ether, tetrahydrofuran (THF), acetone, dimethylformamide (DMF), dimethylsulfoxide (DMSO), pyridine, acetonitrile, benzene, toluene, xylene) in the presence of a dehydrating agent (e.g. $SOCl_2$, $SO_2Cl_2$, $POCl_3$, $PBr_3$, $PCl_5$, polyphophoric acid (PPA)) or a condensating agent (e.g. N,N'-dicyclohexylcarbodiimide (DCC), N-cyclohexyl-N'-morpholinoethylcarbodiimide, N,N'-diisopropylcarbodiimide, $ClCO_2CH_3$, $ClCO_2C_2H_5$, $BrCO_2CH_3$, $(CH_3CO)_2O$, Woodward reagent). etc. The use of an activating agent such as silicon tetrachloride or titanium chloride in an appropriate solvent such as dry pyridine is also favorable. The above reaction is ordinarily carried out at a temperature from room temperature to the refluxing temperature, particularly from about 0 ° to 100° C.

When the acid halide or acid anhydride of the carboxylic acid (II) is reacted with the amine (III), the presence of excess of the amine (III) or a tertiary base such as pyridine in the reaction system is preferred for elimination of hydrogen halide or any other acid as by-produced. Also, there may be adopted the Schotten-Baumann method comprising addition of the acid halide to a mixture of the amine (III) and a base such as sodium hydroxide, sodium acetate, sodium carbonate or potassium carbonate kept at a relatively low temperature while stirring. When the ester of the carboxylic acid (II) is used, it may be reacted with the amine (III) at room temperature or while refluxing for ammonolysis, followed by removal of the by-produced alcohol under distillation. Performance of such reaction in an inert solvent (e.g. benzene, dimethylformamide, dimethylsulfoxide, tetrahydrofuran-hexane) in the presence of a base (e.g. sodium methoxide, n-butyl lithium, sodium hydride) is favorable for increasing the yield. The above reaction is usually carried out at a temperature from room temperature to the refluxing temperature, particularly from about 0° to 100° C.

Another typical procedure for production of the heterocyclic oxy-phenoxyacetic acid derivative (I) is as follows:

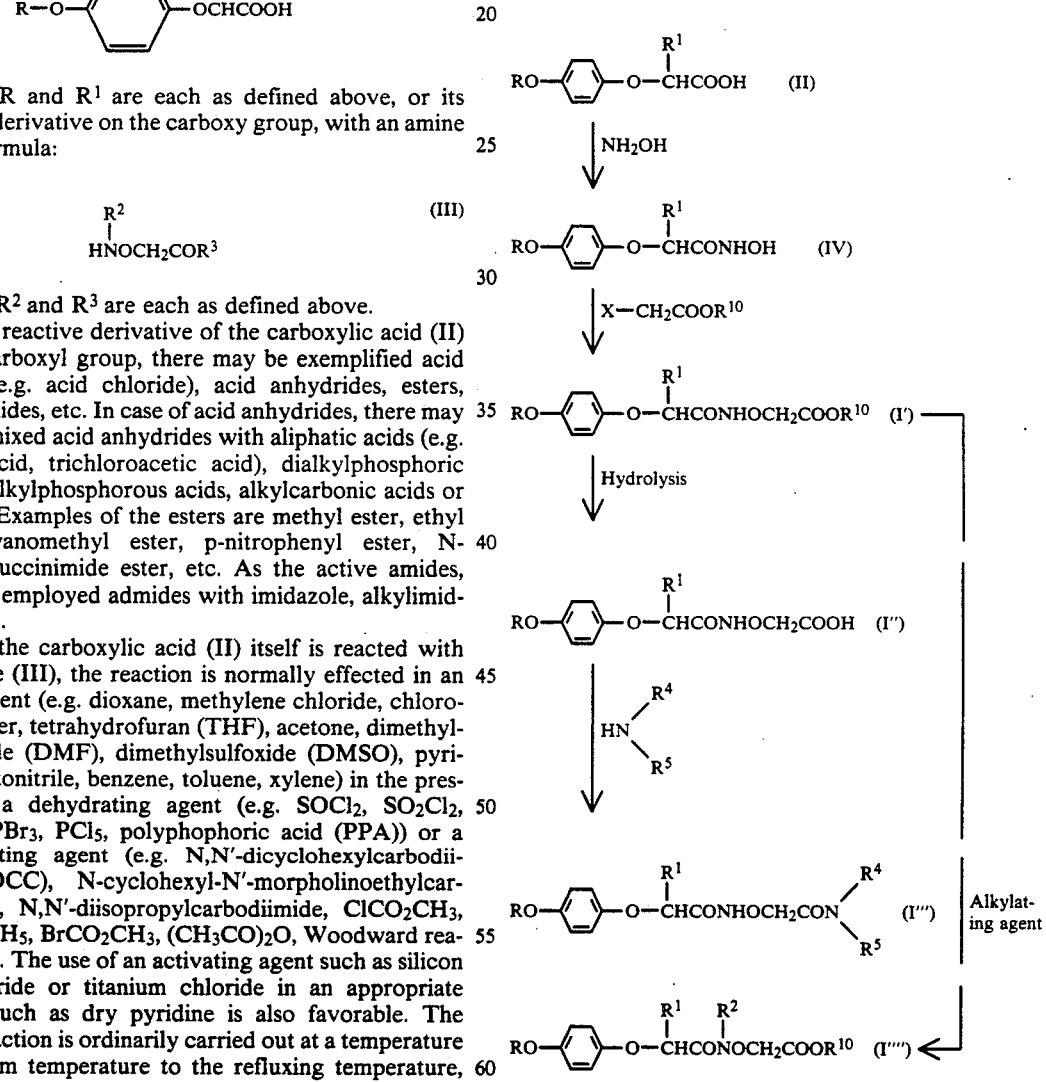

wherein $R^{10}$ is lower alyl, X is halogen, and R, $R^1$, $R^2$, $R^4$ and $R^5$ are each as defined above.

Namely, the carboxylic acid (II) or its reactive derivative at the carboxyl group is reacted with hydroxylamine (hydrochloride) in the presence of a base to give the N-hydroxyamide (IV), which is reacted with an alkyl haloalkanoate in the presence of an acid-eliminating agent to give the phenoxyacetic acid derivative (I'). This phenoxyacetic acid derivative (I') is then hydrolyzed with an alkali, and the resultant phenoxyacetic acid derivative (I'') is reacted with an amine to give the phenoxyacetic acid derivative (I'''). Said phenoxyacetic acid derivative (I') is also reacted with an alkylating agent to give the phenoxyacetic acid derivative (I'''').

Practical embodiments for production of the heterocyclic oxy-phenoxyacetic acid derivative (I) are illustratively shown in the following Reference Examples and Examples.

REFERENCE EXAMPLE 1

Production of methyl aminoxyacetate ($H_2NOCH_2COOCH_3$)

To a suspension of aminoxyacetic acid (½HCl) (5 g) in dry methanol (20 ml), thionyl chloride (12 ml) was dropwise added at −78° C., and the resultant mixture was gradually returned to room temperature and allowed to stand overnight, followed by removal of excess methanol and thionyl chloride by distillation to give methyl aminoxyacetate (hydrochloride) (5.0 g). Yield, 78%.

REFERENCE EXAMPLE 2

Production of N-ethylaminoxyacetamide ($H_2NOCH_2CONHC_2H_5$)

A solution of aminoxyacetic acid (½HCl) (3.5 g) and two droplets of dimethylformamide in thionyl chloride (8 ml) was stirred under reflux for 1 hour, followed by removal of excess thionyl chloride by distillation. The residue was dissolved in dry ether (50 ml), and the resulting solution was dropwise added to 70% aqueous ethylamine (6.2 ml) while cooling with ice. The reaction mixture was gradually returned to room temperature and stirred for 1 hour. The ether layer was separated and concentrated to remove ether. The residue was purified by silica gel chromatography (eluent: ethyl acetate) to give N-ethylaminoxyacetamide (1.2 g). Yield, 31%.

REFERENCE EXAMPLE 3

Production of 4-(3,5-dichloropyridyl-2-oxy)phenol

A suspension of 2,3,5-trichloropyridine (20 g), hydroquinone (25 g) and calcium carbonate (60 g) in dry dimethylsulfoxide (40 ml) was stirred at 90° C. for 6 hours. To the reaction mixture, ether (300 ml) was added, and insoluble materials were removed by filtration. The filtrate was washed with 4% aqueous ammonium chloride, followed by removal of ether by distillation. The residue was purified by silica gel chromatography (eluent: 20% ethyl acetate 80% n-hexane) to give 4-(3,5-dichloropyridyl-2-oxy)phenol (17 g). Yield, 61%.

REFERENCE EXAMPLE 4

Production of ethyl 2-[4-(3,5-dichloropyridyl-2-oxy)phenoxy]propionate

A suspension of 4-(3,5-dichloropyridyl-2-oxy)-phenol (17 g), ethyl DL-2-bromopropionate (13.2 g) and potassium carbonate (12.7 g) in dry methylethylketone (40 ml) was stirred under reflux for 4 hours. After removal of insoluble materials by filtration, the filtrate was concentrated by distillation. The residue was dissolved in dichloromethane, washed with water and concentrated by distillation to remove dichloromethane. The residue was purified by silica gel chromatography (eluent: 2% ethyl acetate: 98% n-hexane) to give ethyl 2-[4-(3,5-dichloropyridyl-2-oxy)phenoxy]propionate (21.4 g). Yield, 95%.

REFERENCE EXAMPLE 5

Production of 2-[4-(3,5-dichloropyridyl-2-oxy)phenoxy]propionic acid

A solution of ethyl 2-[4-(3,5-dichloropyridyl-2-oxy)-phenoxy]propionate (21.4 g) and potassium hydroxide (5.3 g) in ethanol (60 ml) was stirred at room temperature for 1 hour. After removal of ethanol by distillation, the residue was combined with distilled water and made acidic with aqueous hydrochloric acid. The precipitate was collected by filtration and dried to give 2-[4-(3,5-dichloropyridyl-2-oxy)phenoxy]propionic acid (19.8 g). Yield, 96%.

REFERENCE EXAMPLE 6

Production of ethyl 2-(4-hydroxyphenoxy)-propionate

A suspension of hydroquinone (12.2 g), ethyl DL-2-bromopropionate (10 g) and potassium carbonate (50 g) in methylethylketone (100 ml) was stirred under reflux for 5 hours. After removal of insoluble materials by filtration, the filtrate was concentrated by distillation. The residue was dissolved in ethyl acetate, washed with 5% aqueous hydrochloric acid and concentrated to remove ethyl acetate. The residue was purified by silica gel chromatography (eluent: 20% ethyl acetate : 80% n-hexane) to give ethyl 2-(4-hydroxyphenoxy)propionate (3.0 g). Yield, 26%.

REFERENCE EXAMPLE 7

Production of ethyl 2-[4-(3,5-dichloropyridyl-2-oxy)phenoxy]propionate

A suspension of ethyl 2-(4-hydroxyphenoxy)propionate (3.0 g), 2,3,5-trichloropyridine (2.6 g) and potassium carbonate (3.9 g) in dry dimethylsulfoxide (5 ml) was stirred at 90° C. for 5 hours. After removal of insoluble materials by filtration, ether (100 ml) was added thereto. The resultant organic layer was washed with 5% aqueous hydrochloric acid and concentrated to remove ether. The residue was purified by silica gel chromatography (eluent: 2% ethyl acetate 98% n-hexane) to give ethyl 2-[4-(3,5-dichloropyridyl-2-oxy)phenoxy]propionate (2.4 g). Yield, 49%.

REFERENCE EXAMPLE 8

Production of 2-[4-(6-chloro-2-quinoxalinyloxy)phenoxy]propionic acid

Into a mixture of methanol (10 ml) and tetrahydrofuran (14 ml), methyl 2-[4-(6-chloro-2-quinoxalinyloxy)-phenoxy]propionate (0.6 g) was dissolved, and 1N sodium hydroxide solution (2.5 ml) was added thereto. The reaction was carried out at room temperature while stirring for 2 hours. After removal of methanol and tetrahydrofuran by distillation, the aqueous layer was washed with dichloromethane (1 ml), made acidic with conc. hydrochloric acid and extracted with ethyl acetate. The extract was concentrated to remove ethyl acetate to give 2-[4-(6-chloro-2-quinoxalinyloxy)-phenoxy]propionic acid (0.44 g). Yield, 76%.

EXAMPLE 1

Production of
N-methoxycarbonylmethoxy-2-[4-(3,5-dichloro-2-pyridyloxy)phenoxy]propionamide (Compound No. 38)

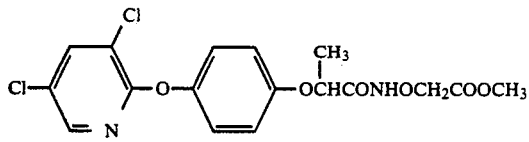

A mixture of 2-[4-(3,5-dichloropyridyl-2-oxy)-phenoxy]propionic acid (11 g), methyl aminoxyacetate (hydrochloride) (4.7 g) and 1-ethyl-3-(3-dimethylaminopropyl)carbodiimide (hydrochloride) (hereinafter referred to as "EDC-HCl") (12.9 g) in dry dichloromethane (15 ml) was stirred at room temperature for 2 hours. The reaction mixture was washed with water and concentrated. The residue was crystallized from a mixture of ethyl acetate and n-hexane to give N-methoxycarbonylmethoxy-2-[4-(3,5-dichloro-2-pyridyloxy)phenoxy]propionamide (10.4 g). Yield 75%.

EXAMPLE 2

Production of
N-ethylcarbamoylmethoxy-2-[4-(3,5-dichloro-2-pyridyloxy)phenoxy]propionamide (Compound No. 3)

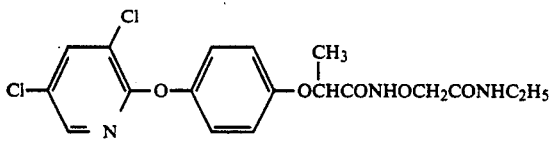

A mixture of 2-[4-(3,5-dichloropyridyl-2-oxy)-phenoxy]propionic acid (1 g), N-ethylaminoxyacetamide (0.43 g) and EDC-HCl (1.2 g) in dry dichloromethane (10 ml) was stirred at room temperature for 2 hours. The reaction mixture was washed with water and concentrated. The residue was crystallized from a mixture of dichloromethane and n-hexane to give N-ethylcarbamoylmethoxy-2-[4-(3,5-dichloro-2-pyridyloxy)phenoxy]propionamide (1.2 g). Yield, 90%.

EXAMPLE 3

Production of
N-hydroxycarbonylmethoxy-2-[4-(3,5-dichloro-2-pyridyloxy)phenoxy]propionamide (Compound No. 37)

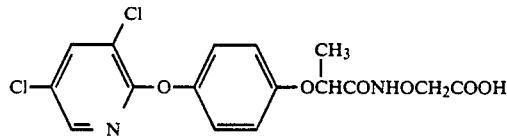

Into a mixture of 1N aqueous sodium hydroxide solution (48 ml) and methanol (300 ml), N-methoxycarbonyl-methoxy-2-[4-(3,5-dichloro-2-pyridyloxy)phenoxy]-propionamide (Compound No. 38 as obtained in Example 1) (9.4 g) was dissolved, and the resultant mixture was stirred at 50° C. for 1 hour. After removal of methanol by distillation, the aqueous layer was made acidic with conc. hydrochloric acid and extracted with ethyl acetate. Removal of the ethyl acetate from the extract by distillation gave N-hydroxy-carbonylmethoxy-2-[4-(3,5-dichloro-2-pyridyloxy)phenoxy]-propionamide (9.0 g). Yield, 98%.

EXAMPLE 4

Production of
N-piperidinocarbamoylmethoxy-2-[4-(3,5-dichloro-2-pyridyloxy)phenoxy]propionamide (Compound No. 14)

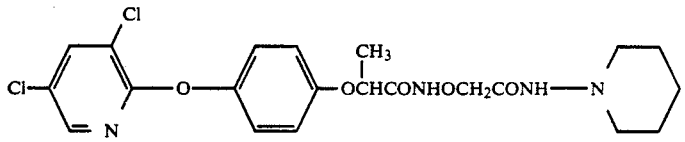

A mixture of N-hydroxycarbonylmethoxy-2-[4-(3,5-dichloro-2-pyridyloxy)phenoxy]propionamide (Compound No. 37 as obtained in Example 3) (0.7 g), 1-aminopiperidine (0.19 g) and EDC-HCl (0.67 g) in dry dichloromethane (5 ml) was stirred at room temperature for 2 hours. The reaction mixture was washed with water and concentrated. The residue was crystallized from a mixture of dichloromethane and n-hexane to give N-piperidinocarbamoylmethoxy-2-[4-(3,5-dichloro-2-pyridyloxy)phenoxy]propionamide (0.56 g). Yield, 73%.

EXAMPLE 5

Production of
N-methoxycarbonylmethoxy-N-methyl-2-[4-(3,5-dichloro-2-pyridyloxy)phenoxy]propionamide (Compound No. 48)

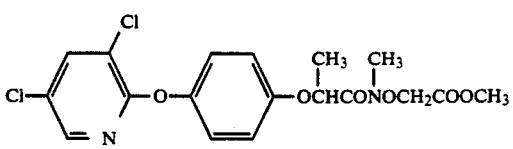

To a solution of N-hydroxycarbonylmethoxy-2-[4-(3,5-dichloro-2-pyridyloxy)phenoxy]propionamide (Compound No. 37 as obtained in Example 3) (0.38 g) in methanol (1 ml), there was added an etheral solution of diazomethane until the yellow color remained, and the resultant mixture was allowed to stand for 10 minutes. The reaction mixture was concentrated under reduced pressure. The residue was purified by silica gel chromatography (eluent: 88% hexane :12% ethyl acetate) to give N-methoxycarbonylmethoxy-N-methyl-2-[4-(3,5-dichloro-2-pyridyloxy)phenoxy]propionamide (0.35 g). Yield, 86%.

In the same manner as above, there are produced the compounds as shown in Table 1.

TABLE 1

$$R-O-\underset{\underset{R^1}{|}}{CH}-\underset{\underset{R^2}{|}}{CON}-OCH_2CO-R^3 \quad (I)$$

| Compound No. | R | R¹ | R² | R³ | Molecular formula (Molecular weight) | Appearance | Melting point (°C.) | Elementary analysis (%) C H N | | |
|---|---|---|---|---|---|---|---|---|---|---|
| 1 | 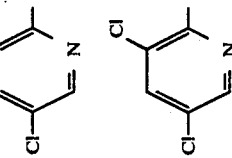 | $CH_3$ | H | $-NH_2$ | $C_{16}H_{15}N_3Cl_2O_5$ (400) | White crystals | 64-65 | Calcd.: 48.02 3.78 10.50<br>Found: 48.11 3.69 10.42 | | |
| 2 | 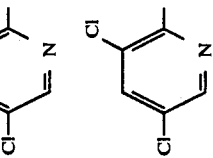 | $CH_3$ | H | $-NHCH_3$ | $C_{17}H_{17}N_3Cl_2O_5$ (414) | White crystals | 138.5-139.5 | Calcd.: 49.29 4.14 10.14<br>Found: 49.19 4.14 10.12 | | |
| 3 | 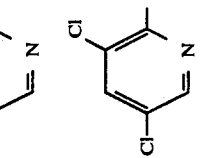 | $CH_3$ | H | $-NHC_2H_5$ | $C_{18}H_{19}Cl_2N_3O_5$ (428) | White crystals | 133.5-135.0 | Calcd.: 50.48 4.47 9.81<br>Found: 50.09 4.51 9.70 | | |
| 4 | 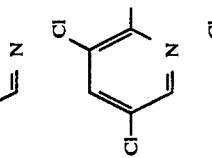 | $CH_3$ | H | $-NHC_3H_7$ | $C_{19}H_{21}Cl_2N_3O_5$ (442) | Transparent oil | | | | |
| 5 | 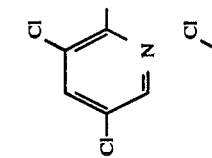 | $CH_3$ | H | $-NHC_4H_9$ | $C_{20}H_{23}Cl_2N_3O_5$ (456) | Transparent oil | | | | |
| 6 | 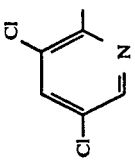 | $CH_3$ | H | $-NH$-t-Bu | $C_{20}H_{23}Cl_2N_3O_5$ (456) | White crystals | 49-50 | Calcd.: 52.64 5.08 9.21<br>Found: 52.69 5.21 8.99 | | |

TABLE 1-continued $$\text{R-O-}\underset{\underset{\text{O-CH-CON-OCH}_2\text{CO-R}^3}{|}}{\overset{\overset{R^1\ R^2}{|\ |}}{\bigcirc}}\quad (I)$$

| Compound No. | R | $R^1$ | $R^2$ | $R^3$ | Molecular formula (Molecular weight) | Appearance | Melting point (°C.) | Elementary analysis (%) C H N |
|---|---|---|---|---|---|---|---|---|
| 7 | 3,5-dichloro-2-methylpyridyl | CH$_3$ | H | —NH—cyclopentyl | C$_{21}$H$_{23}$Cl$_2$N$_3$O$_6$ (483) | Transparent oil | | |
| 8 | 3,5-dichloro-2-methylpyridyl | CH$_3$ | H | —NH—phenyl | C$_{22}$H$_{19}$N$_3$O$_5$Cl$_2$ (475) | White crystals | 130–131 | Calcd.: 55.48 4.02 8.82<br>Found: 55.31 4.13 8.85 |
| 9 | 3,5-dichloro-2-methylpyridyl | CH$_3$ | H | —NHNH$_2$ | C$_{16}$H$_{16}$Cl$_2$N$_4$O$_5$ (415) | White crystals | 134.5–135.3 | Calcd.: 46.28 3.88 13.49<br>Found: 46.00 3.95 13.42 |
| 10 | 3,5-dichloro-2-methylpyridyl | CH$_3$ | H | —NH—N=CHCH$_3$ | C$_{18}$H$_{18}$Cl$_2$N$_4$O$_5$ (441) | White crystals | 151–153 | Calcd.: 48.99 4.11 12.70<br>Found: 48.86 4.17 12.73 |
| 11 | 3,5-dichloro-2-methylpyridyl | CH$_3$ | H | —NH—(2-pyridyl) | C$_{21}$H$_{18}$Cl$_2$N$_4$O$_5$ (477) | White crystals | 136–137 | Calcd.: 52.85 3.80 11.74<br>Found: 52.62 3.81 11.72 |
| 12 | 3,5-dichloro-2-methylpyridyl | CH$_3$ | H | —NH—(3-pyridyl) | C$_{21}$H$_{18}$Cl$_2$N$_4$O$_5$ (477) | Transparent oil | | |

TABLE 1-continued $$R-O-\underset{\underset{R^2}{|}}{\overset{\overset{R^1}{|}}{C}}H-CON-OCH_2CO-R^3 \quad (I)$$

| Compound No. | R | R¹ | R² | R³ | Molecular formula (Molecular weight) | Appearance | Melting point (°C.) | Elementary analysis (%) C H N |
|---|---|---|---|---|---|---|---|---|
| 13 | 3,5-dichloro-2-methyl-pyridin-4-yl-oxy | CH₃ | H | —NH—N⟨morpholine⟩ | C₂₀H₂₂Cl₂N₄O₆ (484) | Transparent oil | | |
| 14 | " | CH₃ | H | —NH—N⟨piperidine⟩ | C₂₁H₂₄Cl₂N₄O₅ (483) | White crystals | 129.0–130.5 | Calcd.: 52.18 5.00 11.59<br>Found: 51.73 4.97 11.41 |
| 15 | " | CH₃ | H | —N(CH₃)₂ | C₁₈H₁₉Cl₂N₃O₅ (428) | White crystals | 121.5–122.0 | Calcd.: 50.48 4.47 9.81<br>Found: 50.44 4.62 9.85 |
| 16 | " | CH₃ | H | —N(C₃H₇)₂ | C₂₂H₂₇N₃Cl₂O₅ (484) | White crystals | 102.5–103.1 | Calcd.: 54.55 5.62 8.68<br>Found: 54.31 5.57 8.71 |
| 17 | " | CH₃ | H | piperidin-1-yl | C₂₁H₂₃Cl₂N₃O₅ (467) | Transparent oil | | |
| 18 | " | CH₃ | H | morpholin-4-yl | C₂₀H₂₁N₃Cl₂O₆ (470) | White crystals | 145.0–146.0 | Calcd.: 51.08 4.50 8.93<br>Found: 50.69 4.56 9.10 |

TABLE 1-continued $$R-O-\underset{\displaystyle \bigcirc}{\phantom{O}}-O-\underset{R^1}{\overset{\phantom{R^2}}{\underset{|}{C}H}}-\underset{\phantom{R^2}}{\overset{R^2}{\underset{|}{C}ON}}-OCH_2CO-R^3 \quad (I)$$

| Compound No. | R | R¹ | R² | R³ | Appearance | Molecular formula (Molecular weight) | Melting point (°C.) | Elementary analysis (%) C H N |
|---|---|---|---|---|---|---|---|---|
| 19 |  | CH₃ | H |  | White crystals | $C_{22}H_{25}Cl_2N_3O_6$ (498) | 149.5–150.5 | Calcd.: 53.02 5.06 8.43<br>Found: 53.12 5.03 8.29 |
| 20 | 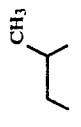 | CH₃ | H |  | White crystals | $C_{22}H_{25}Cl_2N_3O_6$ (498) | 138.5–140.0 | Calcd.: 53.02 5.06 8.43<br>Found: 53.16 4.99 8.50 |
| | (optical isomer of Compound No. 19) | | | | | | | |
| 21 |  | CH₃ | H |  | White crystals | $C_{20}H_{21}Cl_2N_3O_5S$ (486) | 149–150 | Calcd.: 49.39 4.35 8.64<br>Found: 49.20 4.24 8.58 |
| 22 |  | CH₃ | H |  | Transparent oil | $C_{21}H_{24}Cl_2N_4O_5$ (482) | | |
| 23 | 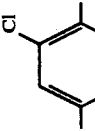 | CH₃ | H | —OC₂H₅ | White crystals | $C_{18}H_{18}Cl_2N_2O_6$ (429) | 105.5–106.5 | Calcd.: 50.37 4.23 6.53<br>Found: 50.00 4.19 6.49 |

TABLE 1-continued $$R-O-\underset{\underset{R^1}{|}}{\overset{\underset{R^2}{|}}{C}}H-CON-OCH_2CO-R^3 \quad (I)$$

(structure shows para-substituted phenyl ring with R-O- on one side)

| Compound No. | R | $R^1$ | $R^2$ | $R^3$ | Molecular formula (Molecular weight) | Appearance | Melting point (°C.) | | Elementary analysis (%) | | |
|---|---|---|---|---|---|---|---|---|---|---|---|
| | | | | | | | | | C | H | N |
| 24 | 3,5-diCl-2-methylpyridinyl | $CH_3$ | H | $-OC_3H_7$ | $C_{19}H_{20}Cl_2N_2O_6$ (443) | White crystals | 78.0-79.0 | Calcd.: Found: | 51.48 51.11 | 4.55 4.63 | 6.32 6.45 |
| 25 | 3,5-diCl-2-methylpyridinyl | $CH_3$ | H | $-OCH(CH_3)_2$ | $C_{19}H_{20}Cl_2N_2O_6$ (443) | White crystals | 121.0-122.5 | Calcd.: Found: | 51.48 51.12 | 4.55 4.52 | 6.32 6.34 |
| 26 | 3,5-diCl-2-methylpyridinyl | $CH_3$ | H | $-O(n)C_4H_9$ | $C_{20}H_{22}Cl_2N_2O_6$ (457) | White crystals | 86.0-87.0 | Calcd.: Found: | 52.53 52.28 | 4.85 4.92 | 6.12 6.32 |
| 27 | 3-Cl-5-CF$_3$-2-methylpyridinyl | $CH_3$ | H | $-OCH_3$ | $C_{18}H_{16}N_2O_6ClF_3$ (448) | White crystals | 101.5-102.1 | Calcd.: Found: | 48.17 47.94 | 3.59 3.64 | 6.24 6.24 |
| 28 | 3-Cl-5-CF$_3$-2-methylpyridinyl | $CH_3$ | H | $-NHCH_3$ | $C_{18}H_{17}N_3O_5ClF_3$ (447) | White crystals | 151.5-152.5 | Calcd.: Found: | 48.28 48.24 | 3.83 3.92 | 9.38 9.28 |
| 29 | 5-CF$_3$-2-methylpyridinyl | $CH_3$ | H | $-OCH_3$ | $C_{18}H_{17}N_2O_6F_3$ (414) | White crystals | 109-110 | Calcd.: Found: | 52.18 52.03 | 4.14 4.22 | 6.76 6.73 |

TABLE 1-continued $$R-O-\underset{\underset{R^1}{|}}{\overset{\underset{R^2}{|}}{C}}H-CON-OCH_2CO-R^3 \quad (I)$$

| Compound No. | R | $R^1$ | $R^2$ | $R^3$ | Molecular formula (Molecular weight) | Appearance | Melting point (°C.) | Elementary analysis (%) | | | |
|---|---|---|---|---|---|---|---|---|---|---|---|
| | | | | | | | | | C | H | N |
| 30 | 2-methyl-5-CF₃-pyridyl | CH₃ | H | —NHCH₃ | C₁₈H₁₈N₃O₅F₃ (413) | White crystals | 133.5–135.0 | Calcd.: Found: | 52.30 52.16 | 4.39 4.46 | 10.17 10.09 |
| 31 | 2-methyl-5-(4-chlorophenyl) pyrimidinyl | CH₃ | H | —NHC₂H₅ | C₂₀H₂₁ClN₄O₅ (432) | Transparent oil | | | | | |
| 32 | 2-methyl-5-(4-chlorophenyl) pyrimidinyl | CH₃ | H | morpholino | C₂₂H₂₃ClN₄O₅ (474) | Transparent oil | | | | | |
| 33 | 3,5-dichloro-2-methylpyridyl | H | H | —OCH₃ | C₁₆H₁₄N₂O₆Cl₂ (401) | White crystals | 96.5–97.5 | Calcd.: Found: | 47.90 47.69 | 3.52 3.63 | 6.98 6.99 |
| 34 | 3,5-dichloro-2-methylpyridyl | H | H | —NHCH₃ | C₁₆H₁₅N₃O₅Cl₂ (400) | White crystals | 121.0–122.5 | Calcd.: Found: | 48.02 47.99 | 3.78 3.80 | 10.50 10.47 |
| 35 | 3-chloro-2-methyl-5-CF₃-pyridyl | H | H | —OCH₃ | C₁₇H₁₄N₂O₆F₃Cl (434) | White crystals | 116–117 | Calcd.: Found: | 46.97 46.84 | 3.25 3.39 | 6.44 6.51 |

TABLE 1-continued $$R-O-\underset{\underset{R^1}{|}}{\overset{\overset{R^2}{|}}{C}}H-CON-OCH_2CO-R^3 \quad (I)$$

| Compound No. | R | $R^1$ | $R^2$ | $R^3$ | Molecular formula (Molecular weight) | Appearance | Melting point (°C.) | Elementary analysis (%) | | | |
|---|---|---|---|---|---|---|---|---|---|---|---|
| | | | | | | | | | C | H | N |
| 36 | 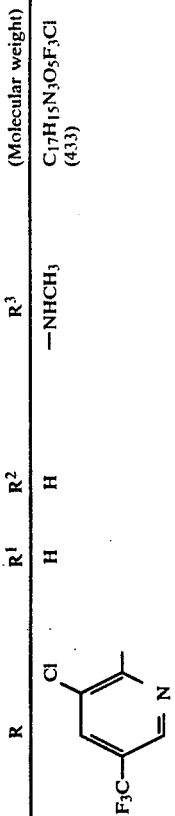 | H | H | —NHCH$_3$ | C$_{17}$H$_{15}$N$_3$O$_5$F$_3$Cl (433) | White crystals | 141–142 | Calcd.: Found: | 47.07 47.12 | 3.49 3.60 | 9.69 9.75 |
| 37 |  | CH$_3$ | H | —OH | C$_{16}$H$_{14}$Cl$_2$N$_2$O$_6$ (401) | White crystals | 137–138 | Calcd.: Found: | 47.90 47.91 | 3.52 3.61 | 6.98 6.96 |
| 38 |  | CH$_3$ | H | —OCH$_3$ | C$_{17}$H$_{16}$Cl$_2$N$_2$O$_6$ (415) | White crystals | 118.5–119.0 | Calcd.: Found: | 49.18 49.15 | 3.88 3.89 | 6.75 6.75 |
| 39 | 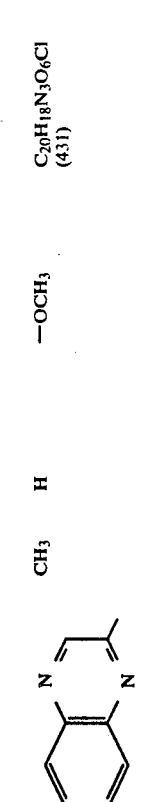 | CH$_3$ | H | —OCH$_3$ | C$_{20}$H$_{18}$N$_3$O$_6$Cl (431) | White crystals | 127.0–128.0 | Calcd.: Found: | 55.63 55.27 | 4.20 4.24 | 9.73 9.62 |
| 40 |  | CH$_3$ | H | —OH | C$_{17}$H$_{15}$N$_2$O$_6$F$_3$ (400) | Transparent oil | | | | | |
| 41 |  | CH$_3$ | H | —O(CH$_2$)$_2$CHCH$_3$<br>                    |<br>                   OCH$_3$ | C$_{21}$H$_{24}$Cl$_2$N$_2$O$_7$ (487.341) | White crystals | 72–75 | | | | |

TABLE 1-continued $$\text{R—O} \overset{R^1}{\underset{R^2}{\text{—CH—CON—OCH}_2\text{CO—R}^3}} \quad (I)$$

| Compound No. | R | R¹ | R² | R³ | Molecular formula (Molecular weight) | Appearance | Melting point (°C.) | Elementary analysis (%) C H N |
|---|---|---|---|---|---|---|---|---|
| 42 | 3,5-dichloropyridin-2-yl | CH₃ | H | —OCH₂C₆H₅ (benzyl) | $C_{24}H_{22}Cl_2N_2O_6$ (505.359) | White crystals | 96–99 | |
| 43 | 3,5-dichloropyridin-2-yl | CH₃ | H | —OCH₂CH₂OC₆H₅ | $C_{24}H_{22}Cl_2N_2O_7$ (521.358) | White crystals | 87–89 | |
| 44 | 3,5-dichloropyridin-2-yl | CH₃ | H | —OCH₂CH₂Cl | $C_{18}H_{17}Cl_3N_2O_6$ (463.705) | White crystals | 86–88 | |
| 45 | 3,5-dichloropyridin-2-yl | CH₃ | H | —OCH₂CH₂Br | $C_{18}H_{17}BrCl_2N_2O_6$ (508.156) | White crystals | 93–96 | |
| 46 | 3,5-dichloropyridin-2-yl | CH₃ | H | —O(CH₂)₂OC₂H₅ | $C_{20}H_{22}Cl_2N_2O_7$ (473.314) | White crystals | 75–77 | |
| 47 | 3,5-dichloropyridin-2-yl | CH₃ | H | —O(CH₂)₂OH | $C_{18}H_{18}Cl_2N_2O_7$ (445.259) | White crystals | 71–74 | |

TABLE 1-continued
$$R-O-\underset{\underset{R^1}{|}}{C}H-CON-\underset{\underset{R^2}{|}}{O}CH_2CO-R^3 \quad (I)$$
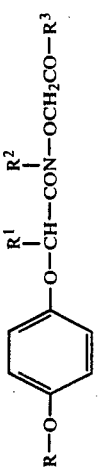
| Compound No. | R | $R^1$ | $R^2$ | $R^3$ | Molecular formula (Molecular weight) | Appearance | Melting point (°C.) | Elementary analysis (%) C H N |
|---|---|---|---|---|---|---|---|---|
| 48 | 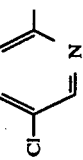 | CH₃ | CH₃ | —OCH₃ | $C_{18}H_{18}Cl_2N_2O_6$ (429.26) | Transparent oil | | |

The $^1$H-NMR ($\alpha$) data of the compounds as shown in Table 1 are given below.

Compound No. 1 (CDCl$_3$) 1.54 (3H, d, J=7.8 Hz), 4.30 (2H, s), 4.69 (1H, q, J=7.8 Hz), 5.78 (2H, bs), 6.81 (2H, d, J=9.0 Hz), 7.03 (2H, d, J=9.0 Hz), 7.60-7.70 (1H, m), 7.80-7.90 (1H, m), 8.00 (1H, bs);

Compound No. 2 (CDCl$_3$): 1.56 (3H, d, J=7.4 Hz), 3.68 (3H, d, J=4.4 Hz), 4.27 (2H, s), 4.74 (1H, q, J=7.4 Hz), 6.81 (2H, d, J=9.0 Hz), 7.03 (2H, d, J=9.0 Hz), 7.60-7.70 (1H, m), 7.80-7.90 (1H, m), 8.00 (1H, bs), 9.63 (1H, bs);

Compound No. 3 (CDCl$_3$): 1.12 (3H, t, J=7.2 Hz), 1.69 (3H, d, J=7.0 Hz), 3.10-3.57 (2H, m), 4.29(2H, s), 4.73 (1H, q, J=7.0 Hz), 6.88 (2H, d, J=9.0 Hz), 7.10 (2H, d, J=9.0 Hz), 7.75 (1H, d, J=2.0 Hz), 7.92 (1H, d, J=2.0 Hz), 8.13 (1H, bs), 9.86 (1H, s);

Compound No. 4 (CDCl$_3$) 0.93 (3H, t, J=6.4 Hz), 1.40-1.76 (2H, m), 1.59 (3H, d, J=6.6 Hz), 3.10-3.43 (2H, m), 4.30 (2H, s), 4.73 (1H, q, J=6.6 Hz), 6.86 (2H, d, J=9.0 Hz), 7.06 (2H, d, J=9.0 Hz), 7.75 (1H, d, J=2.0 Hz), 7.92 (1H, d, J=2.0 Hz), 8.13 (1H, bs), 9.97 (1H, bs);

Compound No. 5 (CDCl$_3$) 1.24 (3H, t, J=7.6 Hz), 1.40-1.76 (4H, m), 1.59 (3H, d, J=6.6 Hz), 3.10-3.43 (2H, m), 4.27 (2H, s), 4.71 (1H, q, J=6.6 Hz), 6.86 (2H, d, J=9.0 Hz), 7.06 (2H, d, J 9.0 Hz), 7.60-7.70 (1H, m), 7.80-7.90 (1H, m), 8.01 (1H, bs), 9.77 (1H, s);

Compound No. 6 (CDCl$_3$): 1.37 (9H, s), 1.58 (3H, d, J=6.6 Hz), 4.13 (2H, s), 4.67 (1H, q, J=6.6 Hz), 6.86 (2H, d, J=9.0 Hz), 7.06 (2H, d, J=9.0 Hz), 7.60-7.70 (1H, m), 7.33 (1H, bs), 7.80-7.90 (1H, m), 9.80 (1H, bs);

Compound No. 7 (CDCl$_3$) 1.50-1.88 (9H, m), 1.58 (3H, d, J=6.6 Hz), 4.21 (2H, s), 4.68 (1H, q, J=6.6 Hz), 6.86 (2H, d, J 9.0 Hz), 7.06 (2H, d, J 9.0 Hz), 7.60-7.70 (1H, m), 7.00 (1H, bs), 7.80-7.90 (1H, m), 8.02 (1H, bs);

Compound No. 8 (CDCl$_3$) 1.59 (3H, d, J=6.6 Hz), 4.38 (2H, s), 4.76 (1H, q, J=6.6 Hz), 6.83-7.90 (1H, m), 9.90 (1H, s), 10.23 (1H, bs);

Compound No. 9 (DMSOd$_6$) 1.43 (3H, d, J=6.6 Hz), 4.00-4.70 (2H, bs), 4.21 (2H, s), 4.65 (1H, q, J=6.6 Hz), 6.80 (2H, d, J=9.0 Hz), 7.00 (2H, d, J=9.0 Hz), 7.97 (1H, d, J=2.4 Hz), 8.11 (1H, d, J=2,4 Hz), 9.17 (1H, s);

Compound No. 10 (DMSOd$_6$) 1.42 (3H, d, J=6.6 Hz), 1.73-1.89 (3H, m), 4,27 (1H, s), 4.60 (1H, s), 4.69 (1H, q, J=6.6 Hz), 6.80 (2H, d, J=9.0 Hz), 7.00 (2H, d, J=9.0 Hz), 7.30 (1H, q, J=5.4 Hz), 7.93-8.00 (1H, m), 8.10-8.17 (1H, m), 11.10-11.23 (1H, bs);

Compound No. 11 (CDCl$_3$) 1.59 (3H, d, J 6.6 Hz), 4.45 (2H, s), 4.74 (1H, q, J=6.6 Hz), 6.79 (2H, d, J =9.0 Hz), 6.71-8.23 (10H, m), 9.84 (1H, s), 10.18 (1H, bs);

Compound No. 12 (CDCl$_3$): 1.60 (3H, d, J 6.6 Hz), 4.43 (2H, s), 4.78 (1H, q, J=6.6 Hz), 6.71-8.74 (11H, m), 10.63 (1H, s);

Compound No. 13 (CDCl$_3$) 1.58 (3H, d, J=6.6 Hz), 2.65-2.88 (4H, m), 3.70-3.85 (4H, m), 4.32 (2H, s), 4.71 (1H, q, J=6.6 Hz), 6.81 (2H, d, J=9.0 HZ), 7.01 (2H, d, J=9.0 Hz), 7.66 (1H, d, J=2.4 Hz), 7.83 (1H, d, J=2.4 Hz), 7.85 (1H, bs), 9.28 (1H, s);

Compound No. 14 (DMSOd6): 1.33-1.50 (9H, m), 2.33-2.66 (4H, m), 4.11 (2H, s), 4.71 (1H, q, J=7.2 Hz), 6.80 (2H, d, J 9.0 Hz), 7.00 (2H, d, J 9.0 Hz), 7.91-8.00 (1H, m), 8.11-8.19 (1H, m), 8.52 (1H, s), 8.90 (1H, s);

Compound No. 15 (CDCl$_3$) 1.59 (3H, d, J 6.6 Hz), 2.86 (3H, s), 2.89 (3H, s), 4,47 (2H, s), 4.68 (1H, q, J=6.6 Hz), 6.82 (2H, d, J=9.0 Hz), 7.01 (2H, d, J=9.0 Hz), 7.93-8.00 (1H, m), 8.10-8.17 (1H, m), 10.09 (1H, bs);

Compound No. 16 (CDCl$_3$) 0.87 (6H, t, J 7.0 Hz), 1.23-1.69 (4H, m), 1.58 (3H, d, J=6.6 Hz), 2.87-3.33 (4H, m), 4,50 (2H, s), 4.67 (1H, q, J=7.0 Hz), 6.81 (2H, d, J=9.0 Hz), 7.01 (2H, d, J=9.0 Hz), 7.91-8.00 (1H, m}, 8.11-8.19 (1H, m), 10.01 (1H, bs);

Compound No. 17 (CDCl$_3$) 1.47-1.70 (4H, m). 1.57 (3H, d, J=7.0 Hz), 4.47 (2H, s), 4.67 (1H, q, J=7.0 Hz), 6.81 (2H, d, J 9.0 Hz), 7.01 (2H, d, J 9.0 Hz), 7.91-8.00 (1H, m), 8.11-8.19 (1H, m), 10.00 (1H, bs);

Compound No. 18 (CDCl$_3$) 1.58 (3H, d, J 6.8 Hz), 2.87-3.70 (8H, m), 4,47 (2H, s), 4.67 (1H, q, J=6.8 Hz), 6.81 (2H, d, J=9.0 Hz), 7.01 (2H, d, J=9.0 Hz), 7.91-8.00 (1H, m), 8.11-8.19 (1H, m), 10.00 (1H, bs);

Compound No. 19 (CDCl$_3$) 1.12 (3H, s), 1.23 (3H. s), 1.58 (3H, d, J=7.0 Hz), 2.30-4.41 (6H, m), 4.51 (2H, s), 4.70 (1H, q, J=7.0 Hz), 6.85 (2H, d, J=9.0 Hz), 7.04 (2H, d, J=9.0 Hz), 7.95-8.04 (1H, m), 8.15-8.23 (1H, m), 10.01 (1H, bs);

Compound No. 20 (CDCl$_3$) 1.12 (3H, s), 1.23 (3H, s), 1.58 (3H, d, J=7.0 Hz), 2.90-4.15 (6H, m), 4.51 (2H, s), 4.70 (1H, q, J=7.0 Hz), 6.85 (2H, d, J=9.0 Hz), r; 7.04 (2H, d, J=9.0 Hz), 7.95-8.04 (1H, m), 8.15-8.23 (1H, m), 10.01 (1H, bs);

Compound No. 21 (CDCl$_3$): 1.58 (3H, d, J 7.0 Hz), 2.48-2.70 (3H, m), 3.46-3.88 (4H, m), 4.50 (2H, s), 4.67 (1H, q, J=7.0 Hz), 6.84 (2H, d, J=9.0 Hz), 7.01 (2H, d, J=9.0 Hz), 7.91-8.00 (1H, m), 8.11-8.19 (1H, m), 10.01 (1H, bs);

Compound No. 22 (CDCl$_3$): 1.59 (3H, d, J=7.0 Hz), 2.27-2.50 (4H, m), 2.30 (3H, s), 3.23-3.63 (4H, m), 4.54 (2H, s), 4.78 (1H, q, J=7.0 Hz), 6.87 (2H, d, J=9.0 Hz), 7.05 (2H, d, J=9.0 Hz), 7.63-7.77 (1H, m), 7.89-7.93 (1H, m), 9.27 (1H, bs);

Compound No 23 (CDCl$_3$): 1.24 (3H, t, J 7.6 Hz), 1.57 (3H, d, J=6.6 Hz), 4.14 (2H, q, J=7.6 Hz), 4.41 (2H, s), 4.67 (1H, q, J=6.6 Hz), 6.72-7.09 (4H, m), 7.61-7.67 (1H, m), 7.81-7.85 (1H, m), 9.59 (1H, bs);

Compound No. 24 (CDCl$_3$): 0.91 (3H, t, J 6.4 HZ), 1.12-1.79 (2H, m), 1.57 (3H, d, J=6.0 Hz), 4.03 (2H, t, J=6.2 Hz), 4.39 (2H, s), 4.65 (1H, q, J=6.0 Hz), 6.68-7.12 (4H, m), 7.57-7.63 (1H, m), 7.76-7.80 (1H, m), 9.53 (1H, bs);

Compound No. 25 (CDCl$_3$): 1.13 (3H, d, J 6.0 Hz), 1.16 (3H, d, J=6.0 Hz), 1.59 (3H, d, J=6.6 Hz), 4.37 (2H, s), 4.66 (1H, dq, J=6.0 Hz), 5.05 (1H, q, J=6.6 Hz), 6.73-7.09 (4H, m), 7.62-7.67 (1H, m), 7.80-7.84 (1H, m), 9.59 (1H, bs);

Compound No. 26 (CDCl$_3$) 0.94 (3H, t, J 6.4 Hz), 1.00-1.76 (4H, m), 1.68 (3H, d, J=6.2 Hz), 4.10 (2H, t, J 6.0 Hz), 4.43 (2H, s), 4.69 (1H, q, J=6.2 Hz), 6.77-7.00 (4H, m), 7.60-7.62 (1H, m), 7.79-7.84 (1H, m), 9.54 (1H, bs);

Compound No. 27 (CDCl$_3$) 1.61 (3H, d, J 6.6 Hz), 3.73 (3H, s), 4.48 (2H, s), 4.72 (1H, q, J=6.6 Hz), 6.91 (2H, d, J 9.0 Hz), 7.15 (2H, d, J 9.0 Hz), 7.92-7.98 (1H, m), 8.18-8.25 (1H, m). 9.60 ((1H, bs);

Compound No 28 (CDCl$_3$): 1.61 (3H, d, J 6.6 Hz), 2.85 (3H, d, J=4.8 Hz), 4.38 (2H, s), 4.76 (1H, q, J =6.6 Hz), 6.89 (2H, d, J=9.0 Hz), 7.12 (2H, d, J=9.0 Hz), 7.94-7.97 (1H, m), 8.04 (1H, bs), 8.19-8.24 (1H, m), 9.84 (1H, bs);

Compound No. 29 (CDCl$_3$): 1.60 (3H, d, J 7.2 Hz), 3.72 (3H, s), 4.47 (2H, s), 4.71 (1H, q, J=7.2 Hz), 6.86-7.20 (5H, m), 7.80-7.99 (1H, m), 8.37-8.43 (1H, m), 9.64 (1H, bs);

Compound No. 30 (CDCl$_3$): 1.60 (3H, d, J 7.2 Hz), 2.70 (3H, d, J=5.4 Hz), 4.28 (2H, s), 4.72(1H, q, J =7.2 Hz), 6.76-7.13 (5H, m), 7.75-7.93 (1H, m), 8.01 (1H, bs), 8.32-8.38 (1H, m), 9.92 (1H, bs);

Compound No. 31 (CDCl$_3$) 1.15 (3H, t, J 7.6 Hz), 1.55 (3H, d, J=6.4 Hz), 3.05-3.54 (2H, m), 4.26 (2H, s), 4.68 (1H, q, J=6.4 Hz), 6.73-8.50 (8H, m), 8.10 (1H, bs), 10.37 (1H, bs);

Compound No. 32 (CDCl$_3$): 1.55 (3H, d, J 6.4 Hz), 3.32-3.65 (8H, m), 4.55 (2H, s), 4.70 (1H, q, J=6.4 Hz), 6.79-8.55 (9H, m), 9.45 (1H, bs);

Compound No. 33 (CDCl$_3$): 3.76 (3H, s), 4.50 (2H, S), 4.54 (2H, s), 6.78-7.16 (4H, m), 7.67-7.70 (1H, m), 7.83-7.90 (1H, m), 9.60 (1H, bs);

Compound No. 34 (CDCl$_3$) 2.82 (3H, d, J 4.2 Hz), 4.34 (2H, s), 4.53 (2H, s), 6.83 (2H, d, J=9.0 Hz), 7.04 (2H, d, J=9.0 Hz), 7.66-7.69 (1H, m), 7.79-7.89 (1H, m), 8.09 (1H, bs);

Compound No. 35 (CDCl$_3$): 3.78 (3H, s), 4.53 (2H, s), 4.57 (2H, s), 6.83-7.20 (4H, m), 7.91-7.97 (1H, m), 8.17-8.27 (1H, m), 9.60 (1H, m);

Compound No. 36 (CDCl$_3$) 2.85 (3H, d, J 4.8 Hz), 4.38 (2H, s), 4.57 (2H, s), 6.80-7.17 (4H, m), 7.90-7.97 (1H, m), 8.00 (1H, bs), 8.17-8.22 (1H, m), 9.97 (1H, bs);

Compound No. 37 (DMSOd6) 1.42 (3H, d, J=6.6 Hz), 4.31 (2H, s), 4.66 (1H, q, J=6.6Hz), 6.74-7.10 (4H, m), 7.93-8.00 (1H, m), 8.09-8.16 (1H, m), 10.00 (1H, bs);

Compound No. 38 (CDCl$_3$): 1.59 (3H, d, J 6.6 Hz), 3.69 (3H, s), 4.43 (2H, s), 4.67 (1H, q, J=6.6 Hz), 6.73-7.09 (4H, m), 7.61-7.67 (1H, m), 7.80-7.85 (1H, m), 9.53 (1H, bs);

Compound No. 39 (CDCl$_3$) 1.61 (3H, d, J 6.4 Hz), 3.69 (3H, s), 4.46 (2H, s), 4.72 (1H, q, J=6.4 Hz), 6.80-7.22 (4H, m), 7.51-7.52 (2H, m), 7.92-7.96 (1H, m), 8.56 (1H, s), 9.66 (1H, bs);

Compound No. 40 (CDCl$_3$-CD30D) 1.58 (3H, d, J=6.4 Hz), 4.38 (2H, s), 4.69 (1H, q, J=6.4 Hz), 6.81-7.10 (5H, m), 7.71-7.90 (1H, m), 8.24-8.33 (1H, m);

Compound No. 48 (CDCl$_3$-TMS): 1.57 (3H, d, J=6.8 Hz), 3.74 (3H, s), 4.10 (3H, s), 4.52 (2H, s), 4.76 (1H, q, J=6.8 Hz), 7.05 (4H, s), 7.75 (1H, d, J=2.4 Hz), 7.95 (1H, d, J=2.4 Hz).

As stated above, the heterocyclic oxy-phenoxyacetic acid derivative (I) shows a remarkable herbicidal activity against a variety of weeds without producing any material phytotoxicity to broad-leaved crop plants. It is advantageous that its toxicity to mammals including human beings is very low. Further, it shows a significant intergeneric selectivity on monocotyledonous plants. Accordingly, it is useful as a herbicide for agriculture.

Examples of monocotyledonous weeds, which the heterocyclic oxy-phenoxyacetic acid derivative (I) can control, are barnyardgrass (*Echinochloa cruss-galli*), barnyardgrass (*Echinochloa oryzicola*), large crabgrass (*Digitaria ciliaris*), violet crabgrass (*Digitaria violascens*), green foxtail (*Setaria viridis*), giant foxtail (*Setaria faberi*), yellow foxtail (*Setaria glauca*), wild oats (*Avena fatua*), water foxtail (*Alopecurus aequalis*), annual bluegrass (*Poa annua*), water paspalum (*Paspalum thunbergii*), cogongrass (*Imperata cylindrica*), whiskeygrass (*Andropogon virginicus*), zebragrass (*Miscanthus sinensis*), etc.

For the practical usage of the heterocyclic oxy-phenoxyacetic acid derivative (I) as the herbicide, it may be formulated with a conventional solid or liquid carrier(s) or diluent(s) into a conventional preparation form chosen from solutions, suspensions, emulsifiable concentrates, wettable powders, granules, dusts, aerosoles, pastes, fumigants, etc. The content of the heterocyclic oxy-phenoxyacetic acid derivative (I) as the active ingredient in such preparation form is normally within a range of about 0.5 to 90% by weight, preferably about 20 to 70% by weight. Examples of the solid carrier or diluent are talc, clay, kaolin, diatomaceous earth, calcium carbonate, potassium chlorate, potassium nitrate, etc. As the liquid carrier or diluent, there are exemplified water, alcohols, aromatic hydrocarbons, ethers, ketones, esters, etc. When desired, such an auxiliary agent as an emulsifier, a spreading agent, a dispersing agent, a suspending agent and a stabilizer may be incorporated into the herbicidal composition. Further, the composition may be used in combination with other herbicides, insecticides, fungicides, fertilizers, plant growth controlling agent, etc.

The dosage of the heterocyclic oxy-phenoxyacetic acid derivative (I) may be appropriately decided. In general, however, it may be from about 1 to 50 grams, preferably from about 2 to 30 grams, per 10 are.

Practical embodiments of the herbicidal composition of the invention and its use are illustratively shown in the following Formulation Examples and Test Examples wherein parts and % are by weight. The compound number of the active ingredient corresponds to the one in Table 1.

Formulation Example 1 (Solution)

Ten parts of Compound No. 3, 70 parts of xylene and 20 parts of polyoxyethylene alkylaryl ether are uniformly mixed to obtain a solution containing 10% of the active ingredient. The solution thus obtained is diluted with water to a designated concentration for practical application.

Formulation Example 2 (Wettable powder)

Forty parts of Compound No. 5, 55 parts of kaolinite (zieclite), 2 parts of sodium alkylbenzenesulfonate and 3 parts of polyoxyethylene alkylaryl ether are mixed well and pulverized to obtain a wettable powder containing 40% of the active ingredient. The wettable powder thus obtained is diluted with water to a designated concentration for practical application.

Formulation Example 3 (Granules)

One part of Compound No. 8, 20 parts of bentonite, 77 parts of clay and 2 parts of sodium dodecylbenzene sulfonate are mixed well while being powdered. The mixture is then kneaded with about 20 parts of water, granulated and dried to obtain granules containing 1% of the active ingredient.

Test Example 1

Pre-emergence application in upland

Seeds of barnyardgrass (*Echinochloa crus-galli*), southern crabgrass, smartweed, slender amaranth, corn, wheat, soybean, cotton, beet, rapeseed and tomato were sowed to a 5 mm depth in a square pot (7.1×7.1 cm) filled with field soil. The designated amount of the test compound was diluted with water and sprayed to the soil at a spray volume of 10 liters per are. The test plants were cultivated in a with water to a designated concentration for practical application.

Formulation Example 2 (Wettable powder)

Forty parts of Compound No. 5, 55 parts of kaolinite (zieclite), 2 parts of sodium alkylbenzenesulfonate and 3 parts of polyoxyethylene alkylaryl ether are mixed well and pulverized to obtain a wettable powder containing 40% of the active ingredient. The wettable powder thus obtained is diluted with water to a designated concentration for practical application.

Formulation Example 3 (Granules)

One part of Compound No. 8, 20 parts of bentonite, 77 parts of clay and 2 parts of sodium dodecylbenzene sulfonate are mixed well while being powdered. The mixture is then kneaded with about 20 parts of water, granulated and dried to obtain granules containing 1% of the active ingredient.

Test Example 1

Pre-emergence application in upland

Seeds of barnyardgrass (*Echinochloa crus-galli*), southern crabgrass, smartweed, slender amaranth, corn, wheat, soybean, cotton, beet, rapeseed and tomato were sowed to a 5 mm depth in a square pot (7.1×7.1 cm) filled with field soil. The designated amount of the test compound was diluted with water and sprayed to the soil at a spray volume of 10 liters per are. The test plants were cultivated in a greenhouse for 20 days, and the herbicidal activity to weeds and the phytotoxicity to crop plants were observed and evaluated according to the following criteria:

| Index | Evaluation |
|---|---|
| 5 | Complete control |
| 4 | severe control |
| 3 | moderate control |
| 2 | mild control |
| 1 | slight control |
| 0 | No control |

The results are shown in Table 2.

TABLE 2

| Test Compound No. | Dosage (g/are) | Herbicidal activity (weed) | | | | Phytotoxicity (crop plant) | | | | | | |
|---|---|---|---|---|---|---|---|---|---|---|---|---|
| | | Barn-yard-grass | Large crab-grass | Smart-weed | Slender amaranth | Corn | Wheat | Soybean | Cotton | Beet | Rape-seed | Tomato |
| 1 | 40 | 5 | 5 | 0 | 0 | | | | | | | |
| | 5 | | | | | 2 | 1 | 0 | 0 | | | |
| | 2.5 | 5 | 5 | | | 1 | 0 | 0 | 0 | | | |
| | 1.2 | 4 | 5 | | | 0 | 0 | 0 | 0 | | | |
| | 0.6 | 2 | 4 | | | 0 | 0 | 0 | 0 | | | |
| 2 | 40 | 5 | 5 | 0 | 0 | | | | | | | |
| | 5 | 5 | 5 | 0 | 0 | 2 | 1 | 0 | 0 | 0 | 0 | 0 |
| | 2.5 | 5 | 5 | 0 | 0 | 2 | 0 | 0 | 0 | 0 | 0 | 0 |
| | 1.25 | 5 | 5 | 0 | 0 | 0 | 0 | 0 | 0 | 0 | 0 | 0 |
| | 0.6 | 3 | 4 | 0 | 0 | 0 | 0 | 0 | 0 | 0 | 0 | 0 |
| 3 | 40 | 5 | 5 | 0 | 0 | | | | | | | |
| | 1.25 | 3 | 4 | | | 0 | 1 | | | | | |
| | 0.6 | 0 | 2 | | | 0 | 0 | | | | | |
| | 0.3 | 0 | 0 | | | 0 | 0 | | | | | |
| 4 | 40 | 5 | 5 | 0 | 0 | | | | | | | |
| | 1.25 | 4 | 4 | | | 0 | 0 | | | | | |
| | 0.6 | 3 | 3 | | | 0 | 0 | | | | | |
| | 0.3 | 2 | 2 | | | 0 | 0 | | | | | |
| 6 | 40 | 5 | 5 | 0 | 0 | | | | | | | |
| | 1.25 | 3 | 3 | | | 0 | 0 | | | | | |
| | 0.6 | 0 | 2 | | | 0 | 0 | | | | | |
| | 0.3 | 0 | 0 | | | 0 | 0 | | | | | |
| 8 | 40 | 5 | 5 | 0 | 0 | | | | | | | |
| | 1.25 | 4 | 3 | | | 0 | 0 | | | | | |
| | 0.6 | 2 | 2 | | | 0 | 0 | | | | | |
| | 0.3 | 0 | 0 | | | 0 | 0 | | | | | |
| 11 | 40 | 5 | 5 | 0 | 0 | | | | | | | |
| | 20 | | | | | | | | | | | |
| | 10 | | | | | | | | | | | |
| | 5 | | | | | | | | | | | |
| | 2.5 | | | | | | | | | | | |
| 16 | 40 | 5 | 5 | 0 | 0 | | | | | | | |
| | 20 | 5 | 5 | 0 | 0 | 3 | 2 | 0 | 0 | 0 | | 0 |
| | 10 | 5 | 5 | 0 | 0 | 2 | 0 | 0 | 0 | 0 | | 0 |
| | 5 | 5 | 5 | 0 | 0 | 1 | 0 | 0 | 0 | 0 | | 0 |
| | 2.5 | 3 | 4 | 0 | 0 | 0 | 0 | 0 | 0 | 0 | | 0 |
| 38 | 40 | 5 | 5 | 0 | 0 | | | | | | | |
| | 5 | 5 | 5 | 0 | 0 | 3 | 2 | 0 | 0 | 0 | | 0 |
| | 2.5 | 5 | 5 | 0 | 0 | 2 | 0 | 0 | 0 | 0 | | 0 |
| | 1.2 | 3 | 4 | | | 0 | 0 | | | | | |
| | 0.6 | 1 | 2 | | | 0 | 0 | | | | | |
| | 0.3 | 0 | 1 | | | 0 | 0 | | | | | |
| | 0.1 | 0 | 0 | | | 0 | 0 | | | | | |
| (a) | 40 | 5 | 5 | 0 | 0 | | | | | | | |
| | 20 | | | | | | | | | | | |
| | 10 | | | | | | | | | | | |
| | 5 | | | | | | | | | | | |
| | 2.5 | | | | | | | | | | | |
| (c) | 40 | 5 | 5 | 0 | 0 | | | 0 | 0 | | | |
| | 2.5 | 5 | 5 | 0 | 0 | | | 0 | 0 | 0 | 0 | 0 |
| | 1.2 | 4 | 5 | 0 | 0 | | | | | | | |
| | 0.6 | 3 | 5 | 0 | 0 | | | | | | | |
| (d) | 40 | 5 | 5 | 0 | 0 | | | | | | | |
| | 0.6 | 2 | 2 | | | 0 | 0 | | | | | |
| | 0.3 | 2 | 2 | | | 0 | 0 | | | | | |
| | 0.15 | 0 | 0 | | | 0 | 0 | | | | | |

TABLE 2-continued

| Test Compound No. | Dosage (g/are) | Herbicidal activity (weed) | | | | Phytotoxicity (crop plant) | | | | | | |
|---|---|---|---|---|---|---|---|---|---|---|---|---|
| | | Barnyard-grass | Large crab-grass | Smart-weed | Slender amaranth | Corn | Wheat | Soybean | Cotton | Beet | Rape-seed | Tomato |
| | 0.08 | 0 | 0 | | | 0 | 0 | | | | | |

Test Example 2

Post-emergence application in upland

Seeds of barnyardgrass (*Echinochloa crus-galli*), southern crabgrass, smartweed and slender amaranth were sowed to a 5 mm depth in a square pot (7.1×7.1 cm) filled with field soil and cultivated in a greenhouse for 7 days until germination of their second-leaves. The designated amount of the test compound was diluted with water and sprayed to the foliage of the test plants at a spray volume of 10 liters per are. The test plants were further cultivated in the greenhouse for 20 days and the herbicidal activity to weeds and the phytotoxicity to crop plants were examined in the same manner as in Test Example 1. The results are shown in Table 3.

TABLE 3

| Test Compound No. | Dosage (g/are) | Herbicidal activity (weed) | | | |
|---|---|---|---|---|---|
| | | Barn-yard-grass | Large crab-grass | Smart-weed | Slender amaranth |
| 1 | 40 | 5 | 5 | 0 | 0 |
| 2 | 40 | 5 | 5 | 1 | 2 |
| 3 | 40 | 5 | 5 | 2 | 2 |
| 4 | 40 | 5 | 5 | 0 | 1 |
| 5 | 40 | 5 | 5 | 0 | 2 |
| 6 | 40 | 5 | 5 | 0 | 0 |
| 7 | 40 | 5 | 5 | 0 | 0 |
| 13 | 40 | 5 | 5 | 0 | 0 |
| 14 | 40 | 5 | 5 | 0 | 0 |
| 15 | 40 | 5 | 5 | | |
| 16 | 40 | 5 | 5 | 2 | 1 |
| 17 | 40 | 5 | 5 | 0 | 0 |
| 18 | 40 | 5 | 5 | | |
| 22 | 40 | 5 | 5 | 0 | 0 |
| 27 | 40 | 5 | 5 | 0 | 0 |
| 28 | 40 | 5 | 5 | 0 | 0 |
| 31 | 40 | 5 | 5 | 2 | 3 |
| 32 | 40 | 5 | 5 | 0 | 2 |
| 38 | 40 | 5 | 5 | 0 | 0 |
| (a) | 40 | 5 | 5 | 3 | 5 |
| (c) | 5 | 5 | 5 | 0 | 0 |
| (d) | 20 | 5 | 5 | 0 | 2 |

Test Example 3

Post-emergence application in upland

Seeds of wild oat, wheat, water foxtail and annual bluegrass were sowed to a 5 mm depth in a square pot (7.1×7.1 cm) filled with field soil and cultivated in a greenhouse kept at 10° to 15° C. for 3 weeks. The designated amount of the test compound was diluted with water and sprayed to the foliage of the test plants at a spray volume of 10 L/are. The test plants were further cultivated in the greenhouse for 3 to 4 weeks and the herbicidal activity was examined in the same manner as in Test Example 1. The results are shown in Table 4.

TABLE 4

| Test Compound No. | Dosage (g/are) | Herbicidal activity | | | |
|---|---|---|---|---|---|
| | | Wild oat | Wheat | Water foxtail | Annual bluegrass |
| 1 | 2.5 | 5 | 2 | | |
| | 1.2 | 5 | 1 | | |
| | 0.6 | 5 | 0 | | |
| | 0.3 | 1 | 0 | | |
| 2 | 2.5 | 5 | 4 | | |
| | 1.2 | 5 | 1 | | |
| | 0.6 | 4–5 | 0 | | |
| | 0.3 | 2 | 0 | | |
| 3 | 2.5 | 5 | 0 | 5 | 4–5 |
| | 1.2 | 5 | 0 | 5 | 4 |
| | 0.6 | 4–5 | 0 | 4 | 3 |
| | 0.3 | 4 | 0 | 3 | 1 |
| 4 | 2.5 | 5 | 3–4 | | |
| | 1.2 | 5 | 2 | | |
| | 0.6 | 4–5 | 1 | | |
| | 0.3 | 1 | 0 | | |
| 5 | 2.5 | 5 | 4 | | |
| | 1.2 | 5 | 2 | | |
| | 0.6 | 4–5 | 1 | | |
| | 0.3 | 1 | 0 | | |
| 7 | 2.5 | | | — | 3–4 |
| | 1.2 | | | — | 2–3 |
| | 0.6 | | | — | 2 |
| | 0.3 | | | — | 2 |
| 12 | 2.5 | 4 | 1 | — | 3 |
| | 1.2 | 3–4 | 1 | — | 2 |
| | 0.6 | 2 | 1 | — | 2 |
| | 0.3 | 1–2 | 0 | — | 0 |
| 15 | 2.5 | 5 | 4–5 | | |
| | 1.2 | 5 | 2 | | |
| | 0.6 | 4–5 | 1 | | |
| | 0.3 | 4–5 | 0 | | |
| 17 | 2.5 | 5 | 1–2 | | |
| | 1.2 | 5 | 1–2 | | |
| | 0.6 | 4 | 1 | | |
| | 0.3 | 3 | 0 | | |
| 18 | 2.5 | 5 | 1 | 5 | 4 |
| | 1.2 | 4–5 | 1 | 5 | 3 |
| | 0.6 | 4–5 | 0 | 4 | 2 |
| | 0.3 | 4–5 | 0 | 3 | 0 |
| 20 | 2.5 | 4 | 0 | | |
| | 1.2 | 3 | 0 | | |
| | 0.6 | 3 | 0 | | |
| | 0.3 | 2–3 | 0 | | |
| 37 | 2.5 | 5 | 1 | | |
| | 1.2 | 4 | 0 | | |
| | 0.6 | 4 | 0 | | |
| | 0.3 | 3 | 0 | | |
| 38 | 2.5 | 5 | 2 | | |
| | 1.2 | 5 | 1 | | |
| | 0.6 | 4–5 | 0 | | |
| | 0.3 | 3 | 0 | | |
| (c) | 2.5 | — | — | | |
| | 1.2 | 5 | 5 | | |
| | 0.6 | 5 | 5 | | |
| | 0.3 | 4 | 4 | | |
| (b) | 2.5 | 5 | 4–5 | — | 4–5 |
| | 1.2 | 5 | 4–5 | — | 4–5 |
| | 0.6 | 5 | 3 | — | 3 |
| | 0.3 | 4 | 2 | — | 0 |

Test Example 4

Pre-emergence application in paddy field

Seeds of barnyardgrass (*Echinochloa oryziocola*) and monochoria sowed in a square pot (7.1×7.1 cm) filled with paddy field soil, and water was poured therein to make a flooded condition. A designated test compound diluted with water was applied to the pot by perfusion, and the test plants were cultivated in a greenhouse for 20 days. The herbicidal activity was examined in the same manner as in Test Example 1. The results are shown in Table 5.

Test Example 5

Post-emergence application in paddy field

Seeds of barnyardgrass (*Echinochloa oryzicola*) and monochoria sowed in a square pot (7.1×7.1 cm) filled with paddy field soil. Water was poured therein to make a flooded condition, and the test plants were cultivated in a greenhouse for 7 days until emergence of the second-leaves. A designated test compound diluted with water was applied to the pot by perfusion, and the test plants were grown in the greenhouse for 20 days. The herbicidal activity was examined in the same manner as in Test Example 1. The results are also shown in Table 5.

TABLE 5

| Test Compound No. | Dosage (g/are) | Pre-emergence treatment | | Post-emergence treatment | |
|---|---|---|---|---|---|
| | | Barn-yard-grass | Mono-choria | Barn-yard-grass | Mono-choria |
| 2 | 40 | 5 | 3 | 5 | 2 |
| 3 | 40 | 5 | 3 | 5 | 3 |
| 4 | 40 | 5 | 3 | 5 | 3 |
| 15 | 40 | 5 | 3 | 5 | 3 |
| 16 | 40 | 5 | 1 | 5 | 0 |
| 18 | 40 | 5 | 3 | 5 | 2 |
| 38 | 40 | 5 | 4 | 5 | 4 |

What is claimed is:

1. A heterocyclic oxy-phenoxyacetic acid derivative of the formula:

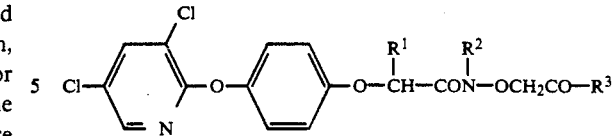

wherein $R^1$ and $R^2$ are each hydrogen or lower alkyl and $R^3$ is $-NR^4R^5$, or $-OR^7$ wherein $R^4$ and $R^5$ are each hydrogen or lower alkyl or, when taken together with the adjacent nitrogen atom, represent a piperidino group, a morpholino group, a thiamorpholino group or a piperazino group, which groups are unsubstituted or are substituted by one or two lower alkyl groups; $R^6$ is lower cycloalkyl, phenyl, pyridyl, piperidino or morpholino, or a group of the formula: $-NR^8R^9$ wherein $R^8$ and $R^9$ are each hydrogen or lower alkyl or, when taken together, represent a lower alkylidene group; and $R^7$ is hydrogen, lower alkyl, phenyl(lower)alkyl, phenoxy(lower)alkyl, halo (lower)alkyl, hydroxy(lower)alkyl or lower alkoxy(lower)alkyl or an agriculturally acceptable salt thereof.

2. A derivative according to claim 1, which is N-ethylcarbamoylmethoxy-2-[4(-3,5-dichloro-2-pyridyloxy)phenoxy]-propionamide.

3. A derivative according to claim 1, which is N-morpholinocarbonylmethoxy-2-[4(-3,5-dichloro-2-pyridyloxy)phenoxy]-propionamide.

4. A derivative according to claim 1, which is N-methoxycarbonylmethoxy-2-[4(-3,5-dichloro-2-pyridyloxy)phenoxy]-propionamide.

5. A herbicidal composition which comprises a herbicidally effective amount of a heterocyclic oxy-phenoxyacetic acid derivative or an agriculturally acceptable salt according to claim 1 as an active ingredient and an agriculturally acceptable inert carrier or diluent.

6. A method for controlling weeds in a field of broad-leaved crop plant, which comprises applying a herbicidally effective amount of a heterocyclic oxy-phenoxyacetic acid derivative or an agriculturally acceptable salt according to claim 1 to the field.

* * * * *